US011506771B2

(12) United States Patent
Yang (10) Patent No.: US 11,506,771 B2
(45) Date of Patent: Nov. 22, 2022

(54) SYSTEM AND METHODS FOR FLASH SUPPRESSION IN ULTRASOUND IMAGING

(71) Applicant: GE Precision Healthcare LLC, Milwaukee, WI (US)

(72) Inventor: Seongho Yang, Seongnam-si (KR)

(73) Assignee: GE Precision Healthcare LLC, Milwaukee, WI (US)

( * ) Notice: Subject to any disclaimer, the term of this patent is extended or adjusted under 35 U.S.C. 154(b) by 542 days.

(21) Appl. No.: 16/581,574

(22) Filed: Sep. 24, 2019

(65) Prior Publication Data
US 2021/0088639 A1   Mar. 25, 2021

(51) Int. Cl.
| | | |
|---|---|---|
| G01S 7/52 | (2006.01) |
| G01S 15/89 | (2006.01) |
| A61B 8/08 | (2006.01) |
| G16H 30/40 | (2018.01) |
| G06N 3/02 | (2006.01) |
| G16H 50/20 | (2018.01) |
| G06N 20/00 | (2019.01) |

(52) U.S. Cl.
CPC ........ *G01S 7/52046* (2013.01); *A61B 8/5246* (2013.01); *G01S 15/8979* (2013.01); *G16H 30/40* (2018.01); *G01S 15/8977* (2013.01); *G06N 3/02* (2013.01); *G06N 20/00* (2019.01); *G16H 50/20* (2018.01)

(58) Field of Classification Search
CPC ......... G06N 3/02; G06N 20/00; A61B 8/5246
See application file for complete search history.

(56) References Cited

U.S. PATENT DOCUMENTS

| | | | | |
|---|---|---|---|---|
| 5,152,292 A | | 10/1992 | Karp | |
| 5,664,575 A | * | 9/1997 | Banjanin | A61B 8/06 600/455 |
| 5,899,864 A | * | 5/1999 | Arenson | G01S 7/52071 600/455 |
| 6,287,258 B1 | * | 9/2001 | Phillips | G01S 7/52046 600/453 |
| 6,402,694 B1 | * | 6/2002 | Bae | G01S 7/52046 600/453 |

(Continued)

FOREIGN PATENT DOCUMENTS

WO   2019034436 A1   2/2019

OTHER PUBLICATIONS

Yoo, Adaptive Clutter Rejection for 3D Color Doppler Imaging: Preliminary Clinical Study, Ultrasound in Med. & Biol., vol. 34, No. 8, pp. 1221-1231, 2008 (Year: 2008).*

(Continued)

*Primary Examiner* — Oommen Jacob
(74) *Attorney, Agent, or Firm* — McCoy Russell LLP (57) ABSTRACT

Methods and systems are provided for color flow ultrasound imaging. In one embodiment, a method comprises acquiring color flow data, detecting, with a neural network, a flash artifact in the color flow data, adjusting an adaptive filter cutoff of a clutter filter based on a classification result of the neural network, filtering, with the clutter filter, the flash artifact from the color flow data, and displaying a color flow image generated from the filtered color flow data. In this way, strong flash artifacts caused by strong tissue movement or probe movement may be dynamically suppressed during color flow ultrasound imaging.

20 Claims, 5 Drawing Sheets

(56) References Cited

U.S. PATENT DOCUMENTS

| | | | |
|---|---|---|---|
| 6,733,455 B2 | 5/2004 | Mo et al. | |
| 6,899,681 B1* | 5/2005 | Phillips | G01S 7/52096 |
| | | | 600/443 |
| 7,203,308 B2* | 4/2007 | Kubota | H04M 9/082 |
| | | | 379/406.01 |
| 7,545,965 B2* | 6/2009 | Suzuki | G06T 7/0012 |
| | | | 382/128 |
| 7,747,551 B2* | 6/2010 | Snyder | G16H 40/63 |
| | | | 706/20 |
| 8,282,560 B2* | 10/2012 | Xiong | A61B 8/06 |
| | | | 600/455 |
| 8,357,094 B2 | 1/2013 | Mo et al. | |
| 9,420,997 B2* | 8/2016 | Wong | G16H 50/30 |
| 10,115,194 B2* | 10/2018 | Niemeijer | G06V 10/82 |
| 10,849,509 B2* | 12/2020 | Zhang | A61B 5/021 |
| 2004/0252759 A1* | 12/2004 | John Winder | H04N 19/87 |
| | | | 375/E7.251 |
| 2008/0021326 A1* | 1/2008 | Bakircioglu | A61B 8/06 |
| | | | 600/454 |
| 2008/0130964 A1* | 6/2008 | Zwirn | G06T 5/40 |
| | | | 382/128 |
| 2008/0214934 A1* | 9/2008 | Lee | A61B 8/481 |
| | | | 600/437 |
| 2018/0107684 A1* | 4/2018 | Kiapour | G06F 16/583 |
| 2018/0177461 A1* | 6/2018 | Bell | A61B 5/7425 |
| 2019/0336107 A1* | 11/2019 | Hope Simpson | G06T 7/0012 |
| 2020/0175652 A1* | 6/2020 | Agarwal | G06T 5/20 |
| 2021/0088639 A1* | 3/2021 | Yang | A61B 8/5269 |

OTHER PUBLICATIONS

Gustafson, Towards Adaptive Split Spectrum Processing, 1995 IEEE Ultrasonics Symposium—729 (Year: 1995).*

Kim Multidimensional Clutter Filter Optimization for Ultrasonic Perfusion Imaging, IEEE Transactions on Ultrasonics, Ferroelectrics, and Frequency Control, vol. 65, No. 11, Nov. 2018 (Year: 2018).*

Khatwani, Energy Efficient Convolutional Neural Networks for EEG Artifact Detection, IEEE 2018 (Year: 2018).*

Cheung, Adaptive Clutter Filter Design for Micro-Ultrasound Color Flow Imaging of Small Blood Vessels, 2010 IEEE International Ultrasonics Symposium Proceedings (Year: 2010).*

Luchies, Deep Neural Networks for Ultrasound Beamforming, IEEE Transactions on Medical Imaging, vol. 37, No. 9, Sep. 2018 (Year: 2018).*

* cited by examiner

SYSTEM AND METHODS FOR FLASH SUPPRESSION IN ULTRASOUND IMAGING

TECHNICAL FIELD

Embodiments of the subject matter disclosed herein relate to ultrasound imaging, and more particularly, to systems and methods for reducing flash artifacts in ultrasound images.

BACKGROUND

Medical ultrasound is an imaging modality that employs ultrasound waves to probe the internal structures of a body of a patient and produce a corresponding image. For example, an ultrasound probe comprising a plurality of transducer elements emits ultrasonic pulses which reflect or echo, refract, or are absorbed by structures in the body. The ultrasound probe then receives reflected echoes, which are processed into an image. Ultrasound images of the internal structures may be displayed on a display device in real time or near real time, which may assist a clinician performing a medical procedure on the patient.

SUMMARY

In one embodiment, a method comprises acquiring color flow data, detecting, with a neural network, a flash artifact in the color flow data, adjusting an adaptive filter cutoff of a clutter filter based on a classification result of the neural network, filtering, with the clutter filter, the flash artifact from the color flow data, and displaying a color flow image generated from the filtered color flow data. In this way, strong flash artifacts caused by strong tissue movement or probe movement may be dynamically suppressed during color flow imaging.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

DETAILED DESCRIPTION

Figure 1:
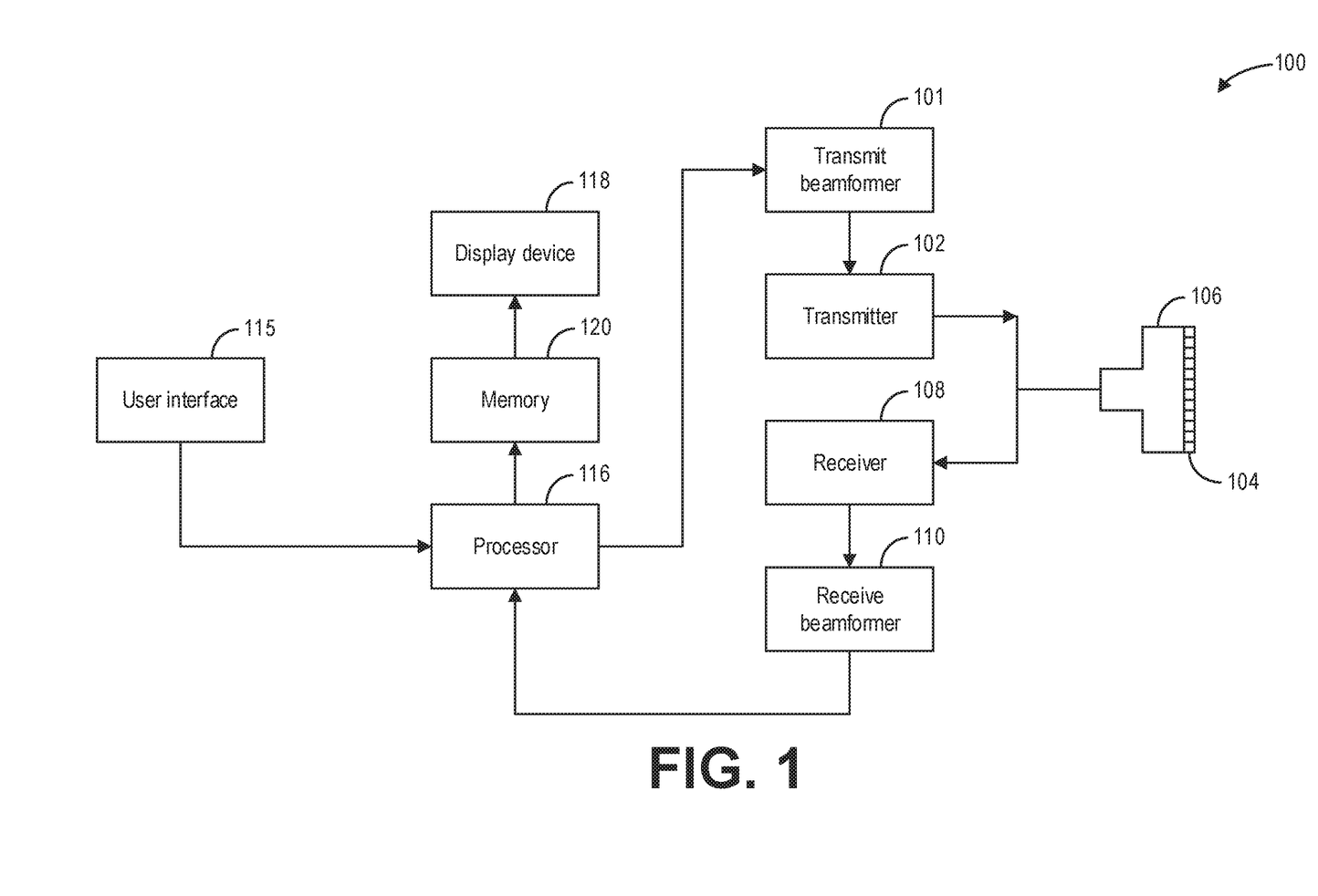
FIG. 1 shows a block diagram of an exemplary embodiment of an ultrasound system.
Figure 2:
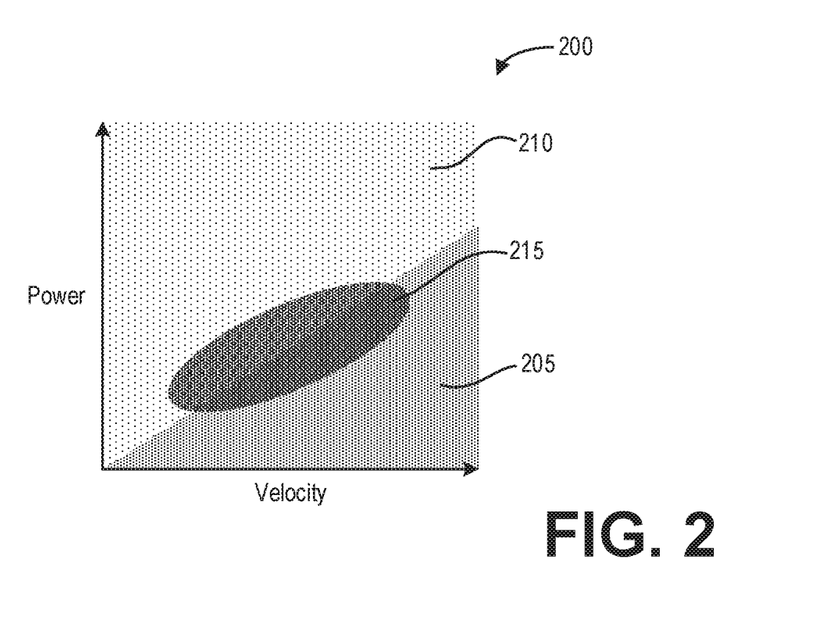
FIG. 2 is a graph illustrating an example parameter space for flash artifacts in color flow image data, according to an exemplary embodiment.

The following description relates to various embodiments for suppressing flash artifacts during color flow ultrasound imaging. An example ultrasound system including an ultrasound probe, a display device, and an imaging processing system are shown in FIG. 1. While color flow ultrasound imaging is focused on imaging and measuring the flow of blood, the tissue and another anatomical features (e.g., bones) surrounding or adjacent to the blood produce strong reflections that are orders of magnitude larger than the backscattered signals from blood. As such reflections, or clutter, would dominate the color flow image data, such clutter is typically removed from the color flow image data so that color flow images can accurately depict the blood flow. While clutter can typically be easily filtered from color flow data, strong flash artifacts caused by tissue movement or probe movement may be more difficult to filter out, as shown in FIG. 2. To suppress such strong flash artifacts, a color flow processing system, such as the color flow processing system shown in FIG. 3, processes the color flow data with a neural network model to adjust an adaptive filter cutoff. The neural network model may comprise a convolutional neural network, as shown in FIG. 4. By adjusting the clutter filter cutoff, a method for color flow imaging, such as the method shown in FIG. 5, may dynamically suppress strong flash artifacts as they arise during color flow imaging.

Referring to FIG. 1, a schematic diagram of an ultrasound imaging system 100 in accordance with an embodiment of the invention is shown. The ultrasound imaging system 100 includes a transmit beamformer 101 and a transmitter 102 that drives elements (e.g., transducer elements) 104 within a transducer array, herein referred to as probe 106, to emit pulsed ultrasonic signals (referred to herein as transmit pulses) into a body (not shown). According to an embodiment, the probe 106 may be a one-dimensional transducer array probe. However, in some embodiments, the probe 106 may be a two-dimensional matrix transducer array probe. As explained further below, the transducer elements 104 may be comprised of a piezoelectric material. When a voltage is applied to a piezoelectric crystal, the crystal physically expands and contracts, emitting an ultrasonic spherical wave. In this way, transducer elements 104 may convert electronic transmit signals into acoustic transmit beams.

After the elements 104 of the probe 106 emit pulsed ultrasonic signals into a body (of a patient), the pulsed ultrasonic signals are back-scattered from structures within an interior of the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. Additionally, transducer element 104 may produce one or more ultrasonic pulses to form one or more transmit beams in accordance with the received echoes.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. In one embodiment, data acquired via ultrasound imaging system 100 may be used to train a machine learning model. A user interface 115 may be used to control operation of the ultrasound imaging system 100, including to control the input of patient data (e.g., patient medical history), to change a scanning or display parameter, to initiate a probe repolarization sequence, and the like. The user interface 115 may include one or more of the following: a rotary element, a mouse, a keyboard, a trackball, hard keys linked to specific actions, soft keys that may be configured to control different functions, and a graphical user interface displayed on a display device 118.

The ultrasound imaging system 100 also includes a processor 116 to control the transmit beamformer 101, the transmitter 102, the receiver 108, and the receive beamformer 110. The processer 116 is in electronic communication (e.g., communicatively connected) with the probe 106. For purposes of this disclosure, the term "electronic communication" may be defined to include both wired and wireless communications. The processor 116 may control the probe 106 to acquire data according to instructions stored on a memory of the processor, and/or memory 120. The processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processor (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment, the demodulation can be carried out earlier in the processing chain. The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay. For example, an embodiment may acquire images at a real-time rate of 7-20 frames/sec. The ultrasound imaging system 100 may acquire 2D data of one or more planes at a significantly faster rate. However, it should be understood that the real-time frame-rate may be dependent on the length of time that it takes to acquire each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data, for example by augmenting the data as described further herein, prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on display device 118. Other embodiments may acquire and display data at different rates. For example, some embodiments may acquire data at a frame-rate of less than 10 Hz or greater than 30 Hz depending on the size of the frame and the intended application. A memory 120 is included for storing processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present invention, data may be processed in different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real time while a procedure (e.g., ultrasound imaging) is being performed on a patient. The video processor module may include a separate image memory, and the ultrasound images may be written to the image memory in order to be read and displayed by display device 118.

In various embodiments of the present invention, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

After performing a two-dimensional ultrasound scan, a block of data comprising scan lines and their samples is generated. After back-end filters are applied, a process known as scan conversion is performed to transform the two-dimensional data block into a displayable bitmap image with additional scan information such as depths, angles of each scan line, and so on. During scan conversion, an interpolation technique is applied to fill missing holes (i.e., pixels) in the resulting image. These missing pixels occur because each element of the two-dimensional block should typically cover many pixels in the resulting image. For example, in current ultrasound imaging systems, a bicubic interpolation is applied which leverages neighboring elements of the two-dimensional block. As a result, if the two-dimensional block is relatively small in comparison to the size of the bitmap image, the scan-converted image will include areas of poor or low resolution, especially for areas of greater depth.

During color flow or color Doppler imaging, blood flow is depicted via color mapping over a grayscale or B-mode ultrasound image of a blood vessel, where the color of a pixel is based on the velocity and/or power of detected echoes from blood. More specifically, the frequency shift of back-scattered ultrasound waves is used to measure the velocity of the back-scattered waves from tissue or blood. The change or shift in back-scattered frequency increases when blood flows towards the probe and decreases when blood flows away from the probe. The Doppler shift may be processed to estimate the average flow velocity, which is displayed using different colors to represent speed and direction of flow. The color flow velocity mode displays hundreds of adjacent sample volumes simultaneously, all color-coded to represent each sample volume's velocity. Furthermore, the power of the back-scattered ultrasound waves or echoes, derived from the amplitude of the echoes, determines the power of the Doppler signal, both of which are related to the number of blood cells in the sample volume. Thus, during color flow imaging, the velocity and a measure of the number of cells moving with the velocity are measured. The velocity and the power measured in a color flow imaging mode may be referred to hereinafter as color flow data.

In addition to detecting the blood flow during color flow imaging, the vibrations of the tissue and vessel in the imaged region are mixed in to the acquired color flow signal. These vibrations, also referred to as clutter, cause flash artifacts which can be suppressed by clutter filtering. However, strong flash artifacts arising from strong tissue movement (caused by heart beats or breathing, for example) or probe movement are difficult to remove via conventional clutter filtering.

FIG. 2 is a graph illustrating an example parameter space 200 for flash artifacts in color flow image data, according to an exemplary embodiment. The parameter region 205 of the parameter space 200 depicts common combinations of velocity and power corresponding and therefore attributable to blood, while the parameter region 210 depicts common combinations of velocity and power corresponding and therefore attributable to clutter. For example, a signal with low velocity but high power, and therefore with parameters in the region 210, is likely caused by slow-moving tissue, whereas a signal with high velocity and low power, and therefore with parameters in the region 205, is likely caused by blood flow.

The clutter may further include strong flash artifacts which occur due to strong tissue movement created by a cardiac motion (e.g., a heartbeat), breathing motion, and so on, or which additionally may occur due to probe movement. The parameter space of such strong flash artifacts is depicted by the region 215, which borders between the region 205 for blood and the region 210 for clutter. Due to this overlap of the strong flash region 215 with the blood region 205 and the clutter region 210 of the parameter space 200, it is difficult to filter out strong flash artifacts with conventional clutter filtering as mentioned hereinabove because some strong flash artifacts are within the blood region 205. Further, such strong flash artifacts may only occur temporarily, or for a small number of ultrasound frames.

Figure 3:
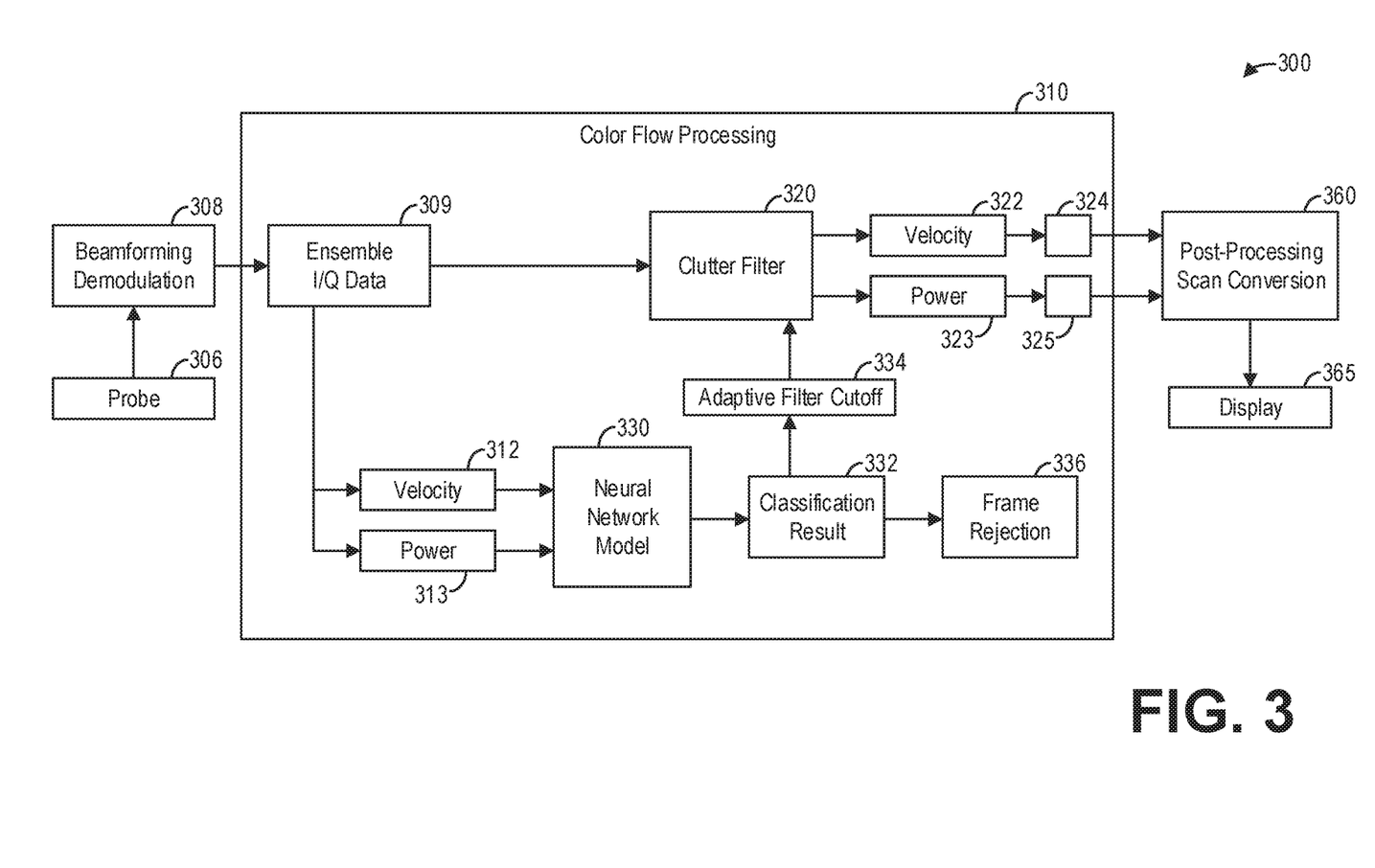
FIG. 3 is a schematic diagram illustrating a system for processing color flow image data, according to an exemplary embodiment.
Figure 4:
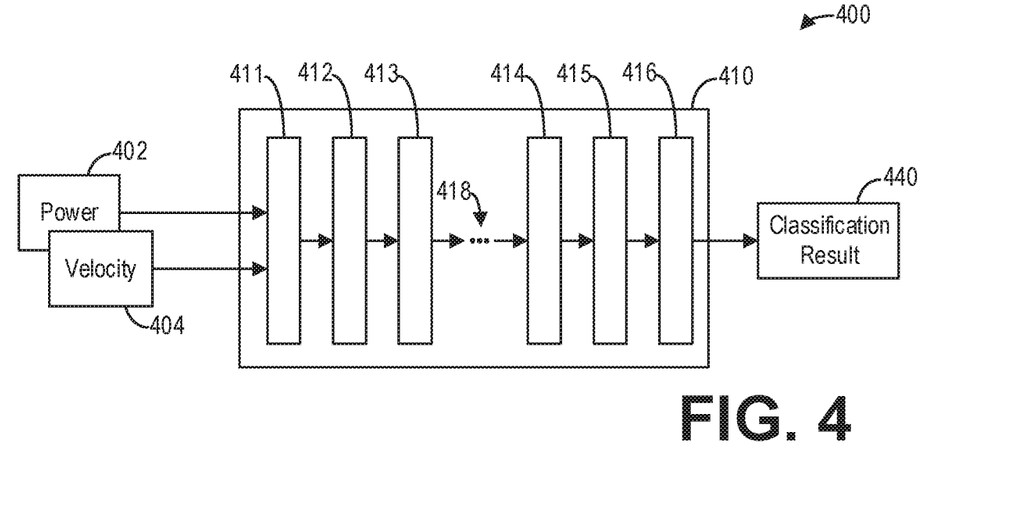
FIG. 4 is a schematic diagram illustrating a layout of a deep learning network for processing color flow image data to detect flash artifacts, according to an exemplary embodiment.

FIG. 3 is a schematic diagram illustrating a system 300 for processing color flow image data with a color flow processing system 310 configured to suppress such strong flash artifacts. The system 300 includes an ultrasound probe 306, a beamforming demodulation module 308, a color flow processing system 310, a post-processing scan conversion module 360, and a display device 365. The system 300 may be implemented in the ultrasound imaging system 100 of FIG. 1. For example, the ultrasound probe 306 may correspond to the probe 106 as well as the receiver 108 and receive beamformer 110, as an illustrative example, while the display device 365 may correspond to the display device 118 of FIG. 1. Similarly, the beamforming demodulation module 308, the color flow processing system 310, and the post-processing scan conversion module 360 may be implemented by the processor 116 and the memory 120 of the ultrasound imaging system 100.

The beamforming demodulation module 308 shifts the RF signals from the probe 306 down in frequency by means of frequency mixers and filters to generate an ensemble of in-phase (I) and quadrature (Q) signals which are centered at a reduced RF frequency but contain the same information bandwidth as the RF signals. Advantageously, the ensemble I/Q data 309 output by the beamforming demodulation module 308 can be digitized and processed at much lower sampling rates due to reduced Nyquist bandwidths.

It should be appreciated that the beamforming demodulation module 308 may also output the ensemble I/Q data 309 to a B-mode processing system (not shown) for processing the ensemble I/Q data 309 into a B-mode or grayscale image, wherein the brightness of a pixel in the B-mode image is based on the detected echo amplitude. Furthermore, while I/Q demodulation is described herein, it should be appreciated that other demodulation techniques, such as Hilbert transform-based demodulation techniques, may be used for beamforming demodulation without departing from the scope of the present disclosure.

The color flow processing system 310 includes a clutter filter 320 for filtering clutter signals from the ensemble I/Q data 309. The clutter filter 320 may comprise a frequency-based filter that reduces the amplitude of the input signal components at one or more given frequencies or frequency bands that correspond to the clutter spectrum as discussed hereinabove with regard to FIG. 2. The clutter filter 320 thus outputs filtered velocity data 322 and filtered power data 323. The filtered velocity data 322 is output at 324 and the filtered power data 323 is output at 325 by the color flow processing system 310 to the post-processing scan conversion module 360. As described hereinabove, the post-processing scan conversion module 360 converts the beam space coordinates of the color flow processed data to display space coordinates to generate a color flow image. The color flow image is then output to the display device 365 for display.

As mentioned above, strong flash artifacts may bypass the clutter filter 320, and so flash artifacts may consequently appear in the color flow images displayed to the user. To robustly identify strong flash artifacts in the color flow image data, the color flow processing system 310 further includes a neural network model 330 configured to receive velocity data 312 and power data 313 of the I/Q data 309 as inputs and to generate a classification result 332 indicating whether a flash artifact is present within the input data. An example neural network model 330 is described further herein with regard to FIG. 4.

Further, in addition to identifying the presence of a flash artifact, the classification result 332 of the neural network model 330 may be used to suppress flash artifacts. For example, the classification result 332 may further indicate a strength of the flash artifact in the input data, which may be used to set a cutoff frequency or an adaptive filter cutoff 334 for the clutter filter 320. For example, the classification result 332 may indicate the highest frequency of the detected flash artifact, so that the adaptive filter cutoff 334 may be set to the highest frequency of the detected flash artifact. The clutter filter 320 may then filter the ensemble I/Q data 309 with the adaptive filter cutoff 334. In this way, the adaptive filter cutoff 334 may be adjusted for each frame according to a corresponding strength of a detected flash artifact, for example by increasing the cutoff 334 for strong flash artifacts or even decreasing the cutoff for weak flash artifacts (i.e., lower frequency flash artifacts) or in the absence of flash artifacts.

Furthermore, the classification result 332 may be provided to a frame rejection module 336 of the color flow processing system 310. The frame rejection module 336 may be configured to reject the ultrasound frame containing a strong flash artifact if the strong flash artifact is too substantial to be filtered out by the clutter filter 320, even with adjustment of the adaptive filter cutoff 334. To that end, the frame rejection module 336 may be configured with a flash threshold such that a frame is rejected when the strength of the flash artifact is above the flash threshold. For frame rejection, the frame may be omitted from display to the user. In other examples, the frame rejection module 336 may down-weight the frame containing the flash artifact in a frame average if a strong flash artifact was not present in the preceding or subsequent ultrasound frames.

It should be understood that color flow processing system 310 shown in FIG. 3 is for illustration, not for limitation. Another appropriate color flow processing system may include more, fewer, or different components.

FIG. 4 is a schematic diagram illustrating an example architecture 400 of a convolutional neural network (CNN) 310 for processing color flow image data to detect flash artifacts, according to an exemplary embodiment. CNN 410 represents one example of a machine learning model according to the current disclosure, wherein the parameters of the CNN 410 may be learned using training data produced according to one or more methods described herein. The power 402 and velocity 404 of the color flow data form an input layer that is input to the CNN 410, and in particular, to a convolution layer 411. The output of the convolution layer 411 is input to a pooling layer 412, the output of which is in turn propagated to a convolution layer 413, and so on through an additional convolution layer 414 and a final pooling layer 415. The output of the final pooling layer 415 is provided to a fully connected layer 416, which outputs the classification result 440. It should be appreciated that additional layers 418 may be included in the CNN 410.

The CNN 410 thus includes a plurality of feature maps or layers (and/or copied feature maps), wherein each feature map may receive input from either an external file, or a previous feature map, and may transform/map the received input to output to produce a next feature map. Each feature map may comprise a plurality of neurons, where in some embodiments, each neuron may receive input from a subset of neurons of a previous layer/feature map, and may compute a single output based on the received inputs, wherein the output may be propagated to a subset of the neurons in a next layer/feature map. A feature map may be described using spatial dimensions, such as length, width, and depth, wherein the dimensions refer to the number of neurons comprising the feature map (e.g., how many neurons long, how many neurons wide, and how many neurons deep, a specified feature map is).

In some embodiments, the neurons of the feature maps may compute an output by performing a dot product of received inputs using a set of learned weights (each set of learned weights may herein be referred to as a filter), wherein each received input has a unique corresponding learned weight, wherein the learned weight was learned during training of the CNN 410.

In some embodiments, the input data of the power 402 and the velocity 404 is pre-processed (e.g., normalized) before being processed by the neural network 410. The weights/parameters of each layer of CNN 410 may be learned during a training process, wherein matched pairs of input and expected output (ground truth output) are fed to CNN 410. Parameters may be adjusted based on a gradient descent algorithm, or other algorithm, until the output of CNN 410 matches the expected output (the ground truth output) within a threshold degree of accuracy.

The weights (and biases) of the convolutional layers in CNN 410 are learned during training. Briefly, a loss function is defined to reflect the difference between the predicted output and the ground truth output. The difference/loss may be back projected to the CNN 410 to update the weights (and biases) of the convolutional layers. A plurality of training data sets, comprising color flow data and corresponding ground truth outputs, such as an indication of whether the color flow data includes a flash artifact as well as a strength of the flash artifact, may be used to train CNN 410.

It will be appreciated that the current disclosure encompasses neural network architectures comprising one or more regularization layers, including batch normalization layers, dropout layers, Gaussian noise layers, and other regularization layers known in the art of machine learning which may be used during training to mitigate overfitting and increase training efficiency while reducing training duration. Regularization layers are used during CNN training and deactivated or removed during post training implementation of the CNN. These layers may be interspersed between the layers/feature maps shown in FIG. 4, or may replace one or more of the shown layers/feature maps.

It should be understood that the architecture and configuration of CNN 410 shown in FIG. 4 is for illustration, not for limitation. Any appropriate neural network can be used, such as U-Net, ResNet, recurrent neural networks, General Regression Neural Network (GRNN), etc. One or more specific embodiments of the present disclosure are described above in order to provide a thorough understanding. The skilled artisan will understand that specific details described in the embodiments can be modified when being placed into practice without deviating the spirit of the present disclosure.

Figure 5:
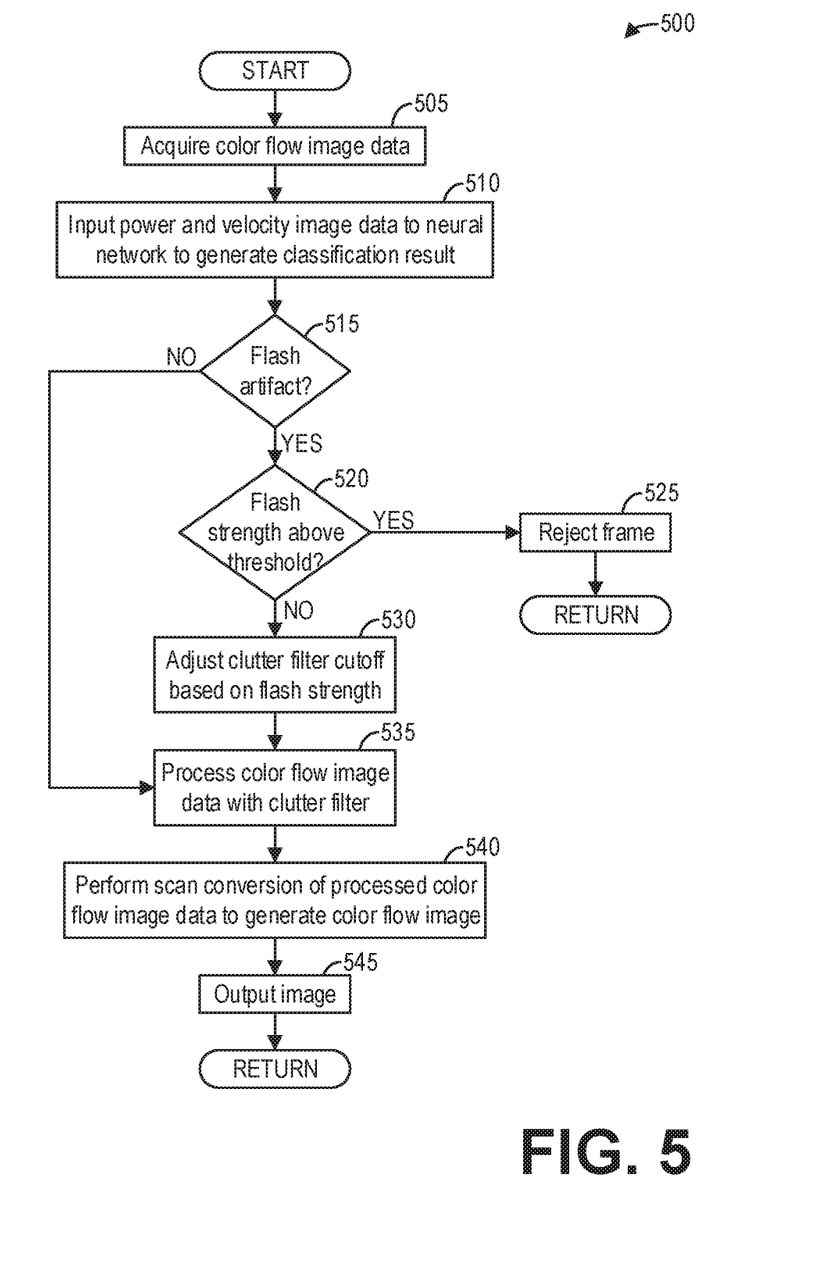
FIG. 5 is a high-level flow chart illustrating an example method for dynamic flash artifact suppression, according to an exemplary embodiment.

FIG. 5 is a high-level flow chart illustrating an example method 500 for dynamic flash artifact suppression. Method 500 may be implemented by one or more of the above disclosed systems, such as the color flow processing system 210 and/or ultrasound imaging system 100.

At 505, method 500 acquires color flow image data via an ultrasound system (e.g., the ultrasound imaging system 100 of FIG. 1). To acquire the images, an ultrasound probe of the ultrasound system (e.g., probe 106 or probe 306) may be controlled to output ultrasound signals (e.g., via energization of the ultrasound transducers of the ultrasound probe) to an imaging subject (such as a patient) and receive the resultant echoes (e.g., where the output acoustic signals are backscattered from the imaging subject). Further, method 500 measures the Doppler shift of the resultant echoes as well as the amplitude to determine the velocity and power, respectively.

At 510, method 500 inputs power and velocity data of the color flow image data to a neural network to generate a classification result. For example, method 500 inputs the power and velocity data to a convolutional neural network such as CNN 410 to generate a classification result 440 indicating whether a flash artifact is present within the color flow image data, as well as the strength of the flash artifact.

At 515, method 500 determines whether the classification result indicates that a flash artifact is present in the color flow image data. If there not a flash artifact ("NO"), method 500 continues to 535. At 535, method 500 processes the color flow image data acquired at 505 with a clutter filter to remove clutter signals. At 540, method 500 performs scan conversion of the processed color flow image data to generate a color flow image. At 545, method 500 outputs the color flow image and then returns.

However, referring again to 515, if there is a flash artifact ("YES"), method 500 proceeds to 520. At 520, method 500 determines whether the flash strength is above a threshold. The threshold is determined based on the capability of the clutter filter. For example, the threshold is determined such that, if the flash strength is at or above the threshold, the clutter filter may not be able to filter the flash artifact from the color flow image data. Thus, if the flash strength is above the threshold ("YES"), method 500 continues to 525. At 525, method 500 rejects the frame. To reject the frame, method 500 omits the frame from being displayed. Alternatively, in some examples, method 500 down-weights the frame in a frame average if the preceding and subsequent frames do not include a strong flash artifact. Method 500 then returns.

Referring again to 520, if the flash strength is below the threshold ("NO"), method 500 continues to 530. At 530, method 500 adjusts a clutter filter cutoff of a clutter filter, such as the adaptive filter cutoff 334 of the clutter filter 320, based on the flash strength. For example, for frequency-based clutter filtering, the clutter filter cutoff is set to the highest frequency of the flash artifact identified by the neural network. Continuing at 535, method 500 processes the color flow image data with the clutter filter and the adjusted clutter filter cutoff. As the clutter filter cutoff is adjusted based on the flash strength, the flash artifact is filtered from the color flow image data.

At 540, method 500 performs scan conversion of the processed color flow image data to generate a color flow image. At 545, method 500 outputs the color flow image, for example to a display device such as the display device 118 or the display 365. As the clutter filter cutoff was adjusted based on the flash strength, the color flow image output at 545 does not include the flash artifact. Method 500 then returns.

A technical effect of the present disclosure includes the display of color flow images without flash artifacts. Another technical effect of the present disclosure includes the prediction of a flash artifact in color flow data. Yet another technical effect of the present disclosure includes the adjustment of a clutter filter cutoff based on a predicted strength of a flash artifact. Another technical effect of the present disclosure includes the rejection of an ultrasound frame containing a flash artifact.

In one embodiment, a method comprises acquiring color flow data, detecting, with a neural network, a flash artifact in the color flow data, adjusting an adaptive filter cutoff of a clutter filter based on a classification result of the neural network, filtering, with the clutter filter, the flash artifact from the color flow data, and displaying a color flow image generated from the filtered color flow data.

In a first example of the method, detecting the flash artifact in the color flow data comprises inputting velocity and power measurements of the color flow data to the neural network to generate the classification result, and the classification result indicates the presence of the flash artifact in the color flow data. In a second example of the method optionally including the first example, the classification result includes a highest frequency of the detected flash artifact, and adjusting the adaptive filter cutoff comprises setting the adaptive filter cutoff to the highest frequency of the detected flash artifact. In a third example of the method optionally including one or more of the first and second examples, adjusting the adaptive filter cutoff includes increasing the adaptive filter cutoff if the classification result indicates the flash artifact is stronger than a previous setting of the adaptive filter cutoff. In a fourth example of the method optionally including one or more of the first through third examples, adjusting the adaptive filter cutoff includes decreasing the adaptive filter cutoff if the classification result indicates the flash artifact is weaker than the previous setting of the adaptive filter cutoff. In a fifth example of the method optionally including one or more of the first through fourth examples, the method further comprises determining that a strength of the flash artifact is above a flash threshold, and rejecting a color flow frame including the flash artifact from being displayed. In a sixth example of the method optionally including one or more of the first through fifth examples, the method further comprises determining that a strength of the flash artifact is above a flash threshold, and down-weighting a color flow frame including the flash artifact in a frame average with preceding and subsequent color flow frames. In a seventh example of the method optionally including one or more of the first through sixth examples, the method further comprises acquiring additional color flow data, not detecting a second flash artifact in the additional color flow data, and filtering the additional color flow data with the clutter filter configured with a default cutoff. In an eighth example of the method optionally including one or more of the first through seventh examples, the neural network comprises a convolutional neural network configured with a plurality of convolutional layers, a plurality of pooling layers, and at least one fully connected layer.

In another embodiment, a method comprises acquiring an ensemble of color flow data, detecting, with a convolutional neural network, a flash artifact in a frame of the ensemble of color flow data, rejecting the frame if a strength of the flash artifact determined by the convolutional neural network is above a flash threshold, otherwise adjusting an adaptive filter cutoff of a clutter filter based on the strength of the flash artifact, filtering, with the clutter filter configured with the adjusted adaptive filter cutoff, the flash artifact from the frame, and displaying a color flow image generated from the filtered frame of the ensemble of color flow data.

In a first example of the method, the method further comprises demodulating the color flow data prior to inputting the ensemble of color flow data to the convolutional neural network. In a second example of the method optionally including the first example, the convolutional neural network is configured with a plurality of convolutional layers, a plurality of pooling layers, and at least one fully connected layer. In a third example of the method optionally including one or more of the first and second examples, the convolutional neural network is trained to map velocity and power data of the color flow data to a probability of a flash artifact being present in the color flow data and a strength of the flash artifact.

In yet another embodiment, a system comprises an ultrasound probe, a memory storing instructions, and a processor communicably coupled to the memory and when executing the instructions, configured to: acquire, via the ultrasound probe, color flow data; detect, with a neural network stored in the memory, a flash artifact in the color flow data; adjust an adaptive filter cutoff of a clutter filter stored in the memory based on a classification result of the neural network; and filter, with the clutter filter, the flash artifact from the color flow data.

In a first example of the system, the system further comprises a display device, and wherein, when executing the instructions, the processor is configured apply scan conversion to the filtered color flow data to generate a color flow image, and output, to the display device, the color flow image. In a second example of the system optionally including the first example, when executing the instructions, the processor is configured to detect the flash artifact in the color flow data by inputting velocity and power measurements of the color flow data to the neural network to generate the classification result, and wherein the classification result indicates the presence of the flash artifact in the color flow data. In a third example of the system optionally including one or more of the first and second examples, the classification result includes a highest frequency of the detected flash artifact, and, when executing the instructions, the processor is configured to adjust the adaptive filter cutoff by setting the adaptive filter cutoff to the highest frequency of the detected flash artifact. In a fourth example of the system optionally including one or more of the first through third examples, when executing the instructions, the processor is configured to increase the adaptive filter cutoff if the classification result indicates the flash artifact is stronger than a previous setting of the adaptive filter cutoff. In a fifth example of the system optionally including one or more of the first through fourth examples, when executing the instructions, the processor is configured to decrease the adaptive filter cutoff if the classification result indicates the flash artifact is weaker than the previous setting of the adaptive filter cutoff. In a sixth example of the system optionally including one or more of the first through fifth examples, when executing the instructions, the processor is configured to determine that a strength of the flash artifact is above a flash threshold, and reject a color flow frame including the flash artifact from being displayed.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method, comprising:
    acquiring color flow data;
    detecting, with a neural network, a flash artifact in the color flow data;
    obtaining a classification result of the neural network that the flash artifact is less than a threshold strength;
    adjusting an adaptive filter cutoff of a clutter filter based on the classification result of the neural network indicating that the flash artifact is less than the threshold strength;
    filtering, with the clutter filter that was adjusted, the flash artifact from the color flow data;
    displaying a color flow image generated from the filtered color flow data;
    obtaining a further classification result of the neural network that a further flash artifact is greater than the threshold strength; and
    rejecting a frame containing the further flash artifact responsive to obtaining the further classification result.

2. The method of claim 1, wherein detecting the flash artifact in the color flow data comprises inputting velocity and power measurements of the color flow data to the neural network to generate the classification result, and wherein the classification result indicates the presence of the flash artifact in the color flow data.

3. The method of claim 1, wherein the classification result includes a highest frequency of the detected flash artifact, and wherein adjusting the adaptive filter cutoff comprises setting the adaptive filter cutoff to the highest frequency of the detected flash artifact.

4. The method of claim 1, wherein adjusting the adaptive filter cutoff includes increasing the adaptive filter cutoff if the classification result indicates the flash artifact is stronger than a previous setting of the adaptive filter cutoff.

5. The method of claim 4, wherein adjusting the adaptive filter cutoff includes decreasing the adaptive filter cutoff if the classification result indicates the flash artifact is weaker than the previous setting of the adaptive filter cutoff.

6. The method of claim 1, further comprising determining that a strength of the flash artifact is above a flash threshold, and rejecting a color flow frame including the flash artifact from being displayed.

7. The method of claim 1, further comprising determining that a strength of the flash artifact is above a flash threshold, and down-weighting a color flow frame including the flash artifact in a frame average with preceding and subsequent color flow frames.

8. The method of claim 1, further comprising acquiring additional color flow data, not detecting a second flash artifact in the additional color flow data, and filtering the additional color flow data with the clutter filter configured with a default cutoff.

9. The method of claim 1, wherein the neural network comprises a convolutional neural network configured with a plurality of convolutional layers, a plurality of pooling layers, and at least one fully connected layer, wherein a power and a velocity of the color flow data form an input provided to one of the plurality of convolutional layers which provides an output to the plurality of pooling layers, wherein a final pooling layer of the plurality of pooling layers provides an output to one of the at least one fully connected layer, which then outputs the classification result.

10. A method, comprising:
acquiring an ensemble of color flow data;
detecting, with a convolutional neural network, a flash artifact in a frame of the ensemble of color flow data;
obtaining a first classification result of the convolutional neural network that a strength of the flash artifact is greater than the threshold strength;
rejecting the frame responsive to the strength of the flash artifact being determined by the convolutional neural network as being above the flash threshold;
obtaining a second classification result of the neural network for a further flash artifact that a strength of the further flash artifact is less than the threshold strength, where the further flash artifact is in in a further frame of the ensemble of color flow data;
adjusting an adaptive filter cutoff of a clutter filter based on the strength of the further flash artifact being less than the threshold strength;
filtering, with the clutter filter configured with the adjusted adaptive filter cutoff, the further flash artifact from the further frame; and
displaying a color flow image generated from the filtered further frame of the ensemble of color flow data.

11. The method of claim 10, further comprising demodulating the color flow data prior to inputting the ensemble of color flow data to the convolutional neural network.

12. The method of claim 10, wherein the convolutional neural network is configured with a plurality of convolutional layers, a plurality of pooling layers, and at least one fully connected layer.

13. The method of claim 12, wherein the convolutional neural network is trained to map velocity and power data of the color flow data to a probability of a flash artifact being present in the color flow data and a strength of the flash artifact.

14. A system, comprising:
an ultrasound probe;
a memory storing instructions; and
a processor communicably coupled to the memory and when executing the instructions, configured to:
acquire, via the ultrasound probe, color flow data;
detect, with a neural network stored in the memory, a flash artifact in the color flow data;
obtain a classification result of the neural network that the flash artifact is less than a threshold strength;
adjust an adaptive filter cutoff of a clutter filter stored in the memory based on the classification result of the neural network;
filter, with the clutter filter, the flash artifact from the color flow data;
obtain a further classification result of the neural network that a further flash artifact is greater than the threshold strength; and
reject a frame containing the further flash artifact responsive to obtaining the further classification result.

15. The system of claim 14, further comprising a display device, and wherein, when executing the instructions, the processor is configured apply scan conversion to the filtered color flow data to generate a color flow image, and output, to the display device, the color flow image.

16. The system of claim 14, wherein, when executing the instructions, the processor is configured to detect the flash artifact in the color flow data by inputting velocity and power measurements of the color flow data to the neural network to generate the classification result, and wherein the classification result indicates the presence of the flash artifact in the color flow data.

17. The system of claim 14, wherein the classification result includes a highest frequency of the detected flash artifact, and wherein, when executing the instructions, the processor is configured to adjust the adaptive filter cutoff by setting the adaptive filter cutoff to the highest frequency of the detected flash artifact.

18. The system of claim 14, wherein, when executing the instructions, the processor is configured to increase the adaptive filter cutoff if the classification result indicates the flash artifact is stronger than a previous setting of the adaptive filter cutoff.

19. The system of claim 18, wherein, when executing the instructions, the processor is configured to decrease the adaptive filter cutoff if the classification result indicates the flash artifact is weaker than the previous setting of the adaptive filter cutoff.

20. The system of claim 14, wherein, when executing the instructions, the processor is configured to determine that a strength of the flash artifact is above a flash threshold, and reject a color flow frame including the flash artifact from being displayed.

* * * * *